(12) United States Patent
Sacko et al.

(10) Patent No.: US 9,222,885 B2
(45) Date of Patent: Dec. 29, 2015

(54) METHOD FOR ASSAYING NUCLEIC ACIDS BY FLUORESCENCE

(75) Inventors: Mory Sacko, Bamako (ML); Nicolas Delacotte, L'Hay les Roses (FR); Mamadou Saliou Bah, Evry (FR); Marc Conti, Palaiseau (FR)

(73) Assignee: BIOCHEMIKON, SAS (FR)

( * ) Notice: Subject to any disclaimer, the term of this patent is extended or adjusted under 35 U.S.C. 154(b) by 1243 days.

(21) Appl. No.: 12/377,146

(22) PCT Filed: Aug. 10, 2007

(86) PCT No.: PCT/IB2007/002316
§ 371 (c)(1),
(2), (4) Date: Jun. 11, 2010

(87) PCT Pub. No.: WO2008/017948
PCT Pub. Date: Feb. 14, 2008

(65) Prior Publication Data
US 2010/0264331 A1    Oct. 21, 2010

Related U.S. Application Data

(60) Provisional application No. 60/836,949, filed on Aug. 11, 2006.

(30) Foreign Application Priority Data

Aug. 11, 2006   (FR) ..................... 06 07309

(51) Int. Cl.
| | | |
|---|---|---|
| G01N 33/48 | (2006.01) | |
| G01N 21/64 | (2006.01) | |
| C12Q 1/68 | (2006.01) | |
| G01J 3/44 | (2006.01) | |
| G06G 7/58 | (2006.01) | |

(52) U.S. Cl.
CPC .............. *G01N 21/6428* (2013.01); *C12Q 1/68* (2013.01); *C12Q 1/6816* (2013.01); *G01J 3/4406* (2013.01); *G01N 2021/6419* (2013.01); *G01N 2021/6421* (2013.01); *G01N 2021/6482* (2013.01)

(58) Field of Classification Search
CPC ........... C12Q 2525/10; C12Q 2525/20; C12Q 2531/10; A61B 5/14; A61B 5/145
See application file for complete search history.

(56) References Cited

U.S. PATENT DOCUMENTS

| | | | | |
|---|---|---|---|---|
| 7,598,390 | B2 * | 10/2009 | Bradford et al. .............. | 548/159 |
| 8,569,477 | B2 * | 10/2013 | Finne ........................... | 536/25.4 |
| 2005/0158722 | A1 | 7/2005 | Whelan et al. | |
| 2006/0047443 | A1 | 3/2006 | Namkoong et al. | |

FOREIGN PATENT DOCUMENTS

| | | |
|---|---|---|
| DE | 199 15 137 | 10/2000 |
| EP | 1632580 | 3/2006 |
| WO | WO-03/070980 | 8/2003 |

OTHER PUBLICATIONS

Barn. Robert A et al: "The use of benzo(a)pyrene diolepoxide-modified DNA 18-20 standards for adduct quantification in 32P-postlabelling to assess exposure to polycyclic aromatic hydrocarbons: Application in bomonitoring study" Mutation Research, vol. 378, No. 1-2, 1997, pp. 41-50, XP002459385.

Nicklas, Janice A et al: "Quantification of DNA in forensic samples." Analytical and Bioanalytical Chemistry, vol. 376, No. 8, Aug. 2003, pp. 1160-1167, XP002421550.

Guan et al: "Determination of nucleic acids based on the fluorescence quenching of Hoechst 33258 at pH 4.5" Analytica Chimica Acta, vol. 570, No. 1, Jun. 7, 2006, pp. 21-28, XP005457530.

Berland, Keith M: "Detection of specific DNA sequences using dual-color two-photon fluorescence correlation spectroscopy." Journal of Biotechnology, vol. 108, No. 2, Mar. 4, 2004, pp. 127.136, XP002459386.

* cited by examiner

*Primary Examiner* — Eric S Dejong
(74) *Attorney, Agent, or Firm* — Merchant & Gould P.C.

(57) ABSTRACT

The invention relates to a method for determining the amount of nucleic acid present in a sample, wherein:—a fluorophore is added to the sample,—fluorescence intensities emitted by the fluorophore at least two emission wavelengths in response to light stimulations at least two excitation wavelengths respectively are measured, and—the amount of nucleic acid present in the sample is deduced from the measured fluorescence intensities.

18 Claims, 10 Drawing Sheets

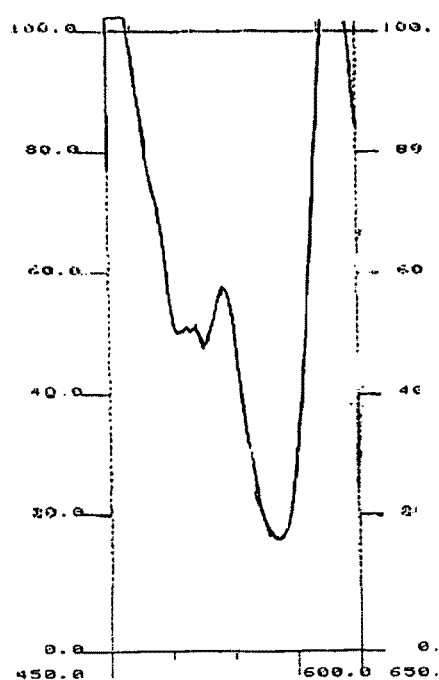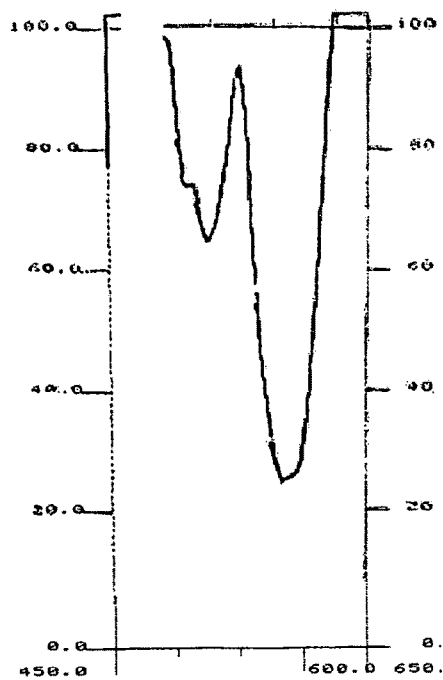
Figure 4                    Figure 5

METHOD FOR ASSAYING NUCLEIC ACIDS BY FLUORESCENCE

This application is the U.S. National Phase of International Patent Application Serial No. PCT/IB2007/002316, filed Aug. 10, 2007, which claims the benefit of U.S. Provisional Patent application Ser. No. 60/836,949, filed Aug. 11, 2006 and French Patent Application serial no. 0607309, filed Aug. 11, 2006, all of which are hereby incorporated by reference in their entireties.

The present invention relates to a fluorimetric method for determining the amount of nucleic acid present in a sample, to a fluorimeter suitable for carrying out said method and to a tray for fluorescence assay of a compound.

The existence of free nucleic acid circulating in the blood has been known for a number of years [Mandel and Métais, 1947; Tan et al., 1966]. Since this time, it has been found using processes such as RIA (radioactive immunoassay) that patients suffering from cancers had a high level of circulating DNA relative to those suffering from benign tumors or relative to healthy subjects [Leon et al., 1977; Shapiro et al., 1983].

However, these recent years, with the development of highly effective molecular biology processes such as real-time PCR, have seen a burgeoning interest in circulating DNA fragments with a view to use as a clinical biological marker.

DNA extracted from the plasma of cancer patients usually has tumoral DNA characteristics [Anker P. et al., 1999] such as strand instability, the presence of specific oncogenes, tumor suppressor genes and microsatellite alterations. The idea that this circulating DNA originated from the tumoral cells was assumed by Kok et al. [De Kok et al., 1997] who reported that the DNA deriving from the tumors, characterised by specific alterations, could be in the serum of patients suffering from a colorectal tumor. Thus, these authors detected certain K-ras point mutations in the DNA of the serum that had previously been identified at the primary tumor. This is why the majority of the studies of circulating DNA focused on the detection of mutations, loss of heterozygosity, microsatellite mutations and the methylation of the DNA extracted from the tumors (tissues) or serum of patients suffering from various types of cancer. The microsatellite mutations and instabilities detected in the free genomic DNA of the serum suggest that it could be a new potential marker, with considerable specificity for monitoring tumors.

More recently, a large number of studies have attempted to use the mere increase in the concentration of genomic or non-genomic, circulating, DNA as a diagnostic marker or a marker of the early development of breast and lung cancer and also for monitoring and inspecting patients who have already received chemotherapy treatment [Sozzi et al., 2001]. This measure would eliminate, or at least reduce, the need for more invasive procedures such as biopsies. It could also be useful in the screening of specific early-stage cancers such as lung [Sozzi et al., 2003], breast [Gal et al., 2004] or prostate [Boddy et al., 2005; Jung et al., 2004] cancer. Finally, it could also be used to complement the analysis of markers commonly used to monitor patients suffering from cancers or undergoing chemotherapy or patients who have undergone a surgical operation, a trauma [Lam et al., 2003] or a myocardial infarction [Chang et al., 2003].

There are basically two types of DNA circulating in the blood:
DNA associated with the circulating nucleated cells; and
DNA circulating freely in the plasma.

Genomic DNA in the serum is fragmented in patients suffering from cancer or having had a myocardial infarction, with the presence of fragments of approximately 100 pairs of bases in the case of carcinomas [Wu et al., 2002] and of approximately 200 pairs of bases in the case of myocardial infarction [Chang et al., 2003]. These fragments are not found in the blood of pathology-free controls in whom, moreover, circulating DNA is found at very low concentrations. Even now, little is known about the mechanism by which DNA is released into the blood stream. Jahr et al. [Jahr et al., 2001] have put forward the hypothesis that apoptotic and necrotic cells are the main sources of this DNA.

There is currently no reference limit value defining the concentration of this circulating DNA in healthy subjects. A plurality of studies have attempted to approximate this threshold but it is quite difficult to compare them as methodologies, and the results obtained differ at many levels. Moreover, the units used vary from study to study: ng/ml; copy number/ml, genome equivalent/ml (amount of DNA contained in a diploid cell estimated at 6.6 picograms/ml), etc.

A plurality of research groups have measured the level of circulating DNA by seeking a potential application in prognosis, in particular by attempting to establish correlations with the conventional diagnosis markers. To date, all of the studies have concurred that the average levels of DNA are substantially higher in cancer patients than in healthy controls, regardless of the serum or plasma used. Nevertheless, the absolute amounts measured vary from study to study. This difference could be linked to the type of cancer analysed and to the various methodologies used. The levels of DNA measured in the plasma are lower than those measured in the serum, as confirmed by large volumes of published data [Thijssen et al., 2002]. With regards to clinical significance, at least two reports describe a correlation between the levels of DNA and known prognosis factors. In (small cell or non-small cell) lung cancers, there is a tight correlation between the levels of plasma DNA and the activity of the LDH of the serum and neuron-specific enolase (NSE), with similar relationships between each marker and patient survival [Fournié et al., 1995]. Similarly, levels of DNA have been correlated with the clinical stage in the case of metastases of the lymph nodes and the size of the tumor in patients suffering from breast cancer [Shao et al., 2001]. Finally, it is important to remember that the fraction of circulating DNA due to the contribution of the tumors varies considerably from patient to patient [Jahr et al., 2001].

A large number of processes for measuring nucleic acids in solution are nowadays available and allow, depending on the method, adaptation to the various needs of clinicians and researchers. These process include, primarily, spectrophotometry [Greenstock et al., 1975]—a method used very commonly in all research laboratories and that has the benefit of being inexpensive but the drawback, which is a major one in clinical practice, of being extremely insensitive: it does not allow the amounts of circulating DNA in patients to be measured.

There are other more sensitive processes but they all have characteristics rendering them more or less difficult to use routinely, partly because they have a common step which is that of extracting the DNA from the biological environment prior to measuring:

Radioimmunoassay processes [Leon et al., 1975] take a relatively long time (several hours per analysis series), have to be carried out in a series of measurements and not sporadically and, above all, require specialist structures and staff authorised to handle radioactive elements.

Competitive PCR [Siebert et al., 1992; Yap et al., 1992], based on comparative display relative to known standards, is the addition of a plurality of processes in series providing detection sensitivity and specificity. These processes are awkward and relatively confidential; routine use thereof in medical analysis laboratories is inconceivable in the future.

Real-time quantitative PCR [Mulder et al., 1994] is the preferred process in the various publications concerned with this problem of measuring circulating DNA. Its benefits are twofold: it is specific to the target DNA to be displayed (in this case, human DNA) and it is nowadays no longer the preserve of research laboratories, as the equipment can be found at a large number of hospitals. Nevertheless, it is not without drawbacks: compulsory extraction, relatively high handling costs, specific equipment which can not be used for large-scale routine analyses, and insufficient sensitivity.

Quantitative fluorimetry [Greenstock et al., 1975]. Although this does not dispense with the extraction step, it allows the free DNA present in the solution to be measured more rapidly and directly. However, the technical conditions under which it is used (microplate, volume reagent, measurement of fluorescence) prevent it from reaching the desired sensitivity limits and do not allow the origin of the detected DNA (human or non-human) to be identified.

The present invention therefore seeks to provide a process for determining the amount of nucleic acid present in a sample that is free from the drawbacks of the existing processes.

The starting point of the invention is therefore the fact the inventors have demonstrated that it is possible to determine the amount of nucleic acid present in a sample by adding a fluorophore to the sample and by determining the fluorescence intensity emitted, in synchronous analysis, or at least two, in particular at least three, differing emission wavelengths in response to excitation at least two, in particular at least three, corresponding wavelengths.

SUMMARY OF THE INVENTION

The present invention relates to a method for determining the amount of nucleic acid present in a sample by fluorescence at least two, preferably at least three wavelengths, wherein:

a fluorophore is added to the sample, fluorescence intensities emitted by the fluorophore at least two, preferably at least three, emission wavelengths in response to light stimulations at least two, preferably at three, excitation wavelengths respectively are measured, and the amount of nucleic acid present in the sample is deduced from the at least two, preferably at least three, measured fluorescence intensities.

In a particular embodiment of the foregoing method, the fluorescence intensities, $I_1$, $I_2$ and $I_3$, emitted by the fluorophore at three emission wavelengths $\lambda_1$, $\lambda_2$ and $\lambda_3$ in response to light stimulations at three excitation wavelengths, $\lambda'_1$, $\lambda'_2$ and $\lambda'_3$ respectively are measured, with $\lambda_1 < \lambda_2 < \lambda_3$ and $\lambda_1$, $\lambda_2$ and $\lambda_3$ being predetermined.

In another particular embodiment of the foregoing method, the amount of nucleic acid is deduced from the following value of F:

$$F = I_2 - \left[ \frac{I_1 - I_3}{\lambda_1 - \lambda_3} \lambda_2 - \frac{\lambda_1 I_3 - \lambda_3 I_1}{\lambda_1 - \lambda_3} \right]$$

In another particular embodiment of the foregoing method, the fluorophore is PICOGREEN® ([N-bis-(3-dimethylaminopropyl)-amino]-4-[2,3-dihydro-3-methyl-(benzo-1,3-thiazol-2-yl)-methylidene]-1-phenyl-quinolinium]+) and the wavelengths are as follows:

$\lambda'_1$=472±10 (preferably ±5) nm $\lambda_1$=502±10 (preferably ±5) nm $\lambda'_2$=496±10 (preferably ±5) nm $\lambda_2$=526±10 (preferably ±5) nm $\lambda'_3$=538±10 (preferably ±5) nm $\lambda_3$=568±10 (preferably ±5) nm Moreover, in another particular embodiment of the foregoing method, the fluorescence intensities $I_1$ and $I_2$, emitted by the fluorophore at two emission wavelengths $\lambda_1$ and $\lambda_2$ in response to light stimulations at two excitation wavelengths, $\lambda_1$, and $\lambda_2$ respectively are measured, $\lambda_1$ and $\lambda_2$ being predetermined.

In this context, the amount of nucleic acid is preferably deduced from the absolute value of the difference between $I_1$ and $I_2$, i.e. from the following value of F:

$$F = |I_2 - I_1|$$

Still in this context, if the fluorophore is PICOGREEN® the wavelengths are as follows:

$\lambda'_1$=472±10 nm $\lambda_1$=502±10 nm, and $\lambda'_2$=496±10 nm $\lambda_2$=526±10 nm, or $\lambda'_1$=496±10 nm $\lambda_1$=526±10 nm, and $\lambda'_2$=538±10 nm $\lambda_2$=568±10 nm More specifically, the amount of nucleic acid in the sample is deduced from the value of F using a calibration curve.

The present invention also relates to a fluorimeter suitable for carrying out a method as defined hereinbefore, characterised in that it comprises:

one or more means for light excitation at two and/or three excitation wavelengths $\lambda'_1$, $\lambda'_2$ and, optionally $\lambda'_3$;

one or more means for measuring the fluorescence intensity, $I_1$, $I_2$ and, optionally $I_3$, emitted at three emission wavelengths $\lambda_1$, $\lambda_2$ and, optionally $\lambda_3$;

a calculator allowing the calculation of a following value F:

$$F = |I_2 - I_1| \text{ and/or } F = I_2 - \left[ \frac{I_1 - I_3}{\lambda_1 - \lambda_3} \lambda_2 - \frac{\lambda_1 I_3 - \lambda_3 I_1}{\lambda_1 - \lambda_3} \right]$$

In a particular embodiment of the foregoing fluorimeter, for three wavelengths, the excitation and emission wavelengths are as follows:

$\lambda'_1$=472±10 (preferably ±5) nm $\lambda_1$=502±10 (preferably ±5) nm $\lambda'_2$=496±10 (preferably ±5) nm $\lambda_2$=526±10 (preferably ±5) nm $\lambda'_3$=538±10 (preferably ±5) nm $\lambda_3$=568±10 (preferably ±5) nm In another particular embodiment of the foregoing fluorimeter, for two wavelengths the excitation and emission wavelengths are as follows:

$\lambda'_1$=472±10 nm $\lambda_1$=502±10 nm, and $\lambda'_2$=496±10 nm $\lambda_2$=526±10 nm, or $\lambda'_1$=496±10 nm $\lambda_1$=526±10 nm, and $\lambda'_2$=538±10 nm $\lambda_2$=568±10 nm The present invention also relates to a tray intended for the fluorescence assay of a compound, comprising a mixing and measuring vessel which is transparent to light at least for the wavelengths used for the fluorescence analysis, the vessel being connected to:
- a reservoir containing a fluorophore, the fluorophore reservoir itself being connected to a reservoir containing a dilution solution; and to
- a reservoir for standardising the volume of a sample containing the compound to be analysed, the standardisation reservoir itself being connected to a well for collecting the sample containing the compound to be analysed.

In a particular embodiment of the tray defined hereinbefore, check valves are positioned:
- between the collection well and the standardisation reservoir, so the collected solution is able to pass only in the direction of the standardisation reservoir;
- between the standardisation reservoir and the mixing and measuring vessel, so the collected solution is able to pass only in the direction of the vessel;
- between the reservoir containing the dilution solution and the fluorophore reservoir, so the dilution solution is able to pass only in the direction of the fluorophore reservoir;
- between the fluorophore reservoir and the mixing and measuring vessel, so the dilution solution is able to pass only in the direction of the vessel.

In another particular embodiment of the tray defined hereinbefore, the compartments consisting of the standardisation reservoir, the mixing and measuring vessel, the fluorophore reservoir and the dilution solution reservoir are made of a sufficiently flexible material to allow liquids contained in the containers to be moved by exerting pressure on the containers.

In another particular embodiment of the tray defined hereinbefore, the fluorophore is PICOGREEN® and the dilution solution is a Tris-Botrate-EDTA (TBE) buffer.

In another particular embodiment of the tray defined hereinbefore, the standardisation reservoir is coupled to a means for selecting nucleic acid molecules contained in the collected solution and having a length of less than 1,000 nucleotides.

DETAILED DESCRIPTION OF THE INVENTION

Nucleic Acid

The nucleic acid may be of natural or synthetic origin and the nucleotides, in particular the ribonucleotides or the deoxyribonucleotides, which it incorporates can be natural or modified. Preferably, the nucleic acid is DNA or RNA, more preferably DNA. Also preferably, the size of the nucleic acid strands is greater than five bases.

Advantageously, the specific quantification of nucleic acids having strands of low molecular weight (length less than 1,000 bases, for example) in a sample, optionally after selection of these nucleic acids using a suitable process, allows quantification of death by apoptosis of the cells, for example, in the organism or the culture from which the sample originates; the value thus measured can be related to the value of the total amount of DNA, optionally measured without any process for selecting strands less than 1,000 bases in size, to provide the percentage of cell death by apoptosis.

Apoptosis can also be quantified by measuring the total nucleic acids and by measuring the nucleic acids of high molecular weight after elimination of the nucleic acids of low molecular weight using a suitable process. The amount of nucleic acids of low molecular weights can then be obtained by subtracting the nucleic acids of high molecular weights.

Optionally, the nucleic acids of low molecular weight can be directly quantified upon their specific selection. The remaining nucleic acids of high molecular weight may then be also measured specifically. Accordingly, the total nucleic may be obtained by addition both quantities.

In order to quantify apoptosis, the specific quantification of the nucleic acids of low molecular weights or high molecular weights and of the total nucleic acids can be carried out by fluorescence, after interaction of the DNA with a fluorophore. The nucleic acids can be captured and/or concentrated in advance using any suitable process.

Apoptosis quantification within the frame of the present invention can proceed in kinetic condition, as experimentation goes along. Indeed, it is not necessary, for example, to stop cell culture to do the measure, since nucleic acids fragments eliminated in the external medium (e.g. culture medium) are measured. Remaining living cells allow continuation of the experimentation. Thus it is possible to repeat measurement a short time after, and so on, as often as necessary. In the same way it is possible to measure apoptosis occurring in humans or in animals, the measure medium will be here any type of biological sample.

Thus, it is possible to conceive numerous application fields: such as the medical field, experimental protocols on animals, or cell cultures . . . . Nucleic acids fragments may be measured in any type of fluids, naturals or not.

One field particularly concerns pharmacological studies, on animals or on cell cultures. Are notably encompassed:
- Testing the lethality of a drug;
- Establishing the cell death induction mode, e.g. necrosis or apoptosis;
- Defining in the experimental conditions which are applied, the time before the first cell death occurs, while other cells stay alive, allowing the continuation of the experimentation.

Another field concerns scientific research on cell culture. It is in fact possible to study effect on cell death of:
- the stimulation or inactivation of metabolic pathways, or
- experimental conditions used.

Yet, another field concerns experimental protocol on animals, for testing the effects of:
- drugs on random cell death,
- induced cell death, or
- experimental conditions.

In addition to all that was describe above, it is interesting to quantify apoptosis in the monitoring or follow up of patients suffering of pathologies inducing cell death, to diagnose their pathologies or to follow up their treatment efficiency.

More generally, the application fields are those where it is necessary to know if cell death occurs, the death induction mode, the delay before its occurrence and the duration of the effect studied. Thus, the amount of nucleic acids which has been determined with the method as defined above is preferably used in the context of cellular death characterization.

Sample

The sample can be of natural or synthetic origin, mineral or organic. Preferably, the sample is a biological sample or a biological sample derivative. More preferably, the sample is derived from a biological sample by dilution. The biological sample may, for example, be of animal, in particular human, or vegetable origin.

Also preferably, the biological sample is selected from the group consisting of cell cultures, whole blood, serum, plasma, formed elements of the blood, erythrocytes, urine, faeces, cerebrospinal fluid, sperm, a puncture fluid, an expectora, saliva, bronchial and alveolar fluids, pus, genital secretions, amniotic fluids, gastric fluids, bile, pancreatic fluid, a tissue biopsy, hair, skin and teeth, and lymphatic fluids.

Also preferably, the sample originates from a patient having undergone a physio-pathological situation wherein cellular disruption may have occurred. In particular the sample originates from a patient selected from the group consisting of a patient suffering or suspected of suffering from a cancer, a patient undergoing chemotherapy, a patient having undergone a surgical operation, a traumatised patient and a patient having undergone a myocardial infarction.

Preferably, nucleic acids contained in the biological sample originate from a cell lysis of physiological or pathological origin, in particular nucleic acids originate from apoptotic cells.

The sample is particularly preferably plasma diluted 20 to 400 times.

Advantageously, the method according to the invention allows quantification of a nucleic acid within any desired sample without prior purification of the nucleic acid.

Fluorophore

The term "fluorophore" refers to a compound which is liable to emit light in response to light excitation.

In the invention, the fluorophore is preferably liable to interact with the nucleic acids by establishing therewith weak or strong interactions or chemical bonds.

Generally, a distinction may be drawn between the fluorophores interacting with the nucleic acids:
  intercalating agents, such as ethidium bromide, propidium iodide or PICOGREEN®;
  agents binding to the minor groove of double-stranded DNA, such as DAPI and Hoechst reagent (for example, Hoechst 33258, Hoechst 34580);
  the various agents interacting with the nucleic acids, such as acridine orange, 7-AAD, LDS 751 and hydroxystilbanidine.

Other examples include fluorophores selected from the group consisting of fluorophores from the SYBR (chemically reactive), TOTO (cyanine dimer), TO-PRO (cyanine monomers), SYTO (penetrating the cells) and SYTOX (not penetrating the cells) families.

Preferably, the fluorophore is a nucleic acid intercalating agent.

The term "nucleic acid intercalating agent" refers to a fluorophore liable to become inserted between the bases forming the nucleic acid chain. Intercalating agents are well known to a person skilled in the art.

Thus, the inventors have, in particular, shown that PICOGREEN®, ethidium bromide, the reagent Hoechst 33258, acridine orange, POPO®, TOTO® and SYBR® allowed the quantification of nucleic acids using the method of the invention.

Preferably, the fluorophore is therefore selected from the group consisting of PICOGREEN®, ethidium bromide, the reagent Hoechst 33258, acridine orange, POPO®, TOTO® and SYBR®.

More preferably, the fluorophore is PICOGREEN® or 2-[N-bis-(3-dimethylaminopropyl)-amino]-4-[2,3-dihydro-3-methyl-(benzo-1,-3-thiazol-2-yl)-methylidene]-1-phenyl-quinolinium]+).

PICOGREEN® is, in particular, sold by Molecular Probes. It is, in particular, characterised in U.S. Pat. No. 5,863,753. In the foregoing process, the PICOGREEN® of the PICOGREEN® dsDNA quantitation kit (Molecular Probes) is preferably used in a dilution from about 1/5,000 to about 1/80,000, in particular in a dilution of about 1/20,000.

When Ethydium bromide is used, the following excitation and emission wavelengths can be used in the above defined method and fluorimeter:
  For three wavelengths:
    $\lambda'_1=475\pm10$ nm $\lambda_1=550\pm10$ nm
    $\lambda'_2=520\pm10$ nm $\lambda_2=595\pm10$ nm
    $\lambda'_3=560\pm10$ nm $\lambda_3=635\pm10$ nm
  For two wavelengths:
    $\lambda'_1=475\pm10$ nm $\lambda_1=550\pm10$ nm
    $\lambda'_2=520\pm10$ nm $\lambda_2=595\pm10$ nm, or
    $\lambda'_1=520\pm10$ nm $\lambda_1=595\pm10$ nm
    $\lambda'_2=560\pm10$ nm $\lambda_2=635\pm10$ nm When Hoechst 33258 is used, the following excitation and emission wavelengths can be used in the above defined method and fluorimeter:
  For three wavelengths:
    $\lambda'_1=315\pm10$ nm $\lambda_1=435\pm10$ nm
    $\lambda'_2=350\pm10$ nm $\lambda_2=470\pm10$ nm
    $\lambda'_3=395\pm10$ nm $\lambda_3=515\pm10$ nm
  For two wavelengths:
    $\lambda'_1=315\pm10$ nm $\lambda_1=435\pm10$ nm
    $\lambda'_2=350\pm10$ nm $\lambda_2=470\pm10$ nm, or
    $\lambda'_1=350\pm10$ nm $\lambda_1=470\pm10$ nm
    $\lambda'_2=395\pm10$ nm $\lambda_2=515\pm10$ nm When SyBr green II is used, the following excitation and emission wavelengths can be used in the above defined method and fluorimeter:
  For three wavelengths:
    $\lambda'_1=450\pm10$ nm $\lambda_1=475\pm10$ nm
    $\lambda'_2=485\pm10$ nm $\lambda_2=510\pm10$ nm
    $\lambda'_3=525\pm10$ nm $\lambda_3=550\pm10$ nm
  For two wavelengths:
    $\lambda'_1=450\pm10$ nm $\lambda_1=475\pm10$ nm
    $\lambda'_2=485\pm10$ nm $\lambda_2=510\pm10$ nm, or
    $\lambda'_1=485\pm10$ nm $\lambda_1=510\pm10$ nm
    $\lambda'_2=525\pm10$ nm $\lambda_2=550\pm10$ nm When Popo 1 is used, the following excitation and emission wavelengths can be used in the above defined method and fluorimeter:
  For three wavelengths:
    $\lambda'_1=415\pm10$ nm $\lambda_1=437\pm10$ nm
    $\lambda'_2=435\pm10$ nm $\lambda_2=457\pm10$ nm
    $\lambda'_3=475\pm10$ nm $\lambda_3=497\pm10$ nm
  For two wavelengths:
    $\lambda'_1=415\pm10$ nm $\lambda_1=437\pm10$ nm
    $\lambda'_2=435\pm10$ nm $\lambda_2=457\pm10$ nm, or
    $\lambda'_1=435\pm10$ nm $\lambda_1=457\pm10$ nm
    $\lambda'_2=475\pm10$ nm $\lambda_2=497\pm10$ nm Synchronous Fluorescence The term "synchronous fluorescence" refers to a fluorimetric process well known to a person skilled in the art in which the two monochromators for receiving the emitted and excitation light are moved simultaneously in order to measure a set of signals corresponding to excitation and emission light, the wavelengths of which are set apart from each other by a constant interval, for example 30 nm. Synchronous fluorescence is, in particular, defined by Lloyd (1971) "Synchronised excitation of fluorescence emission spectra" *Nature*

*physical Science* 231:64-5 and by Ficheux et al. (1991) "La spectrofluorescence synchrone: théorie et applications" Toxicorama 3:1:8-13.

In the method defined hereinbefore, the two or three fluorescence intensities can be measured by synchronous fluorescence or, once the excitation and emission wavelengths have been determined, simply by measuring the two or three intensities of light emitted for the emission wavelengths determined in response to the given excitation wavelengths.

Thus, $\lambda_1$, $\lambda_2$ and, optionally, $\lambda_3$ can be determined by synchronous fluorescence as being points marking variations in the slope of the synchronous spectrum, in particular inflection points or breaking points in the slope of the synchronous spectrum.

It will be understood that a slope breaking point marks the limit between a new slope, which is statistically different from that of the background as is defined by the preceding values, and an average slope value on the points preceding the peak; allowance must also be made for the variability of the points around this average.

More specifically, if three wavelengths are taken as the basis, $\lambda_2$ represents an emission wavelength for which a fluorescence emission intensity peak is observed, this peak being surrounded by two inflection or gradient breaking points corresponding to $\lambda_1$ and $\lambda_3$.

The manner in which the wavelengths $\lambda_1$, $\lambda_2$, $\lambda_3$, $\lambda'_1$, $\lambda'_2$ and $\lambda'_3$ are determined from a synchronous fluorescence spectrum is set out in the following example for the particular case of PICOGREEN®. Briefly, $\lambda_1$, $\lambda_2$, and $\lambda_3$ may, more specifically, correspond respectively:

- to an inflection point of a single curve representing the synchronous fluorescence spectrum of a solution of nucleic acid and the fluorophore if the reading is taken using a SHIMADZU RF 535-type fluorimeter;
- to a break in the gradient of a single curve representing the synchronous fluorescence spectrum of a solution of nucleic acid and the fluorophore if the reading is taken using an SAFAS Xenius-type fluorimeter;

Advantageously, the method according to the invention allows the phenomenon of Rayleigh interference to be limited or prevented.

Alternatively, if two wavelengths are taken as the basis, either $\lambda_1$ or $\lambda_2$ represents an emission wavelength for which a fluorescence emission intensity peak is observed and the other represents an emission wavelength for which an inflection point or a breaking point in the slope directly preceding or following said emission intensity peak is observed. FIGS. 15 and 16 illustrate the choice of $\lambda_1$ and $\lambda_2$. Preferably, one of $\lambda_1$ and $\lambda_2$ represents an emission wavelength for which a fluorescence emission intensity peak is observed and the other represents an emission wavelength for which an inflection point or a breaking point in the slope directly preceding said emission intensity peak is observed.

Although the use of just two wavelengths is less precise than the use of three wavelengths, it also allows the phenomenon of Rayleigh interference to be limited or prevented while at the same time being easy to carry out.

Fluorimeter

With regard to the fluorimeter according to the invention, the power of the excitation bulb is preferably such as to allow, at the excitation wavelengths, a low concentration of DNA, of about 2.5 ng/ml, to be read with precision of less than 10%. Preferably the band width of the monochrometer used does not exceed +/−5 nm. The emission light, in particular that emitted at 90° relative to the direction of the emission light, is preferably captured by a suitable system and directed toward to an emission monochrometer in order to select the wavelengths specific to the measurement.

The value of F is preferably calculated by the computer using an algorithm stored in its memory. Moreover, the fluorimeter according to the invention is preferably equipped with a system allowing the storage of data such as the calibration curves for each measurement group. Also preferably, the fluorimeter according to the invention provides the amount of nucleic acid contained in the sample after the calculation and using the stored calibration curves.

Furthermore, the fluorimeter according to the invention is preferably equipped with a system for displaying the results and also a system for generating and exporting data such as a printer (or a facility for connecting a printer). Moreover, also preferably, the fluorimeter is capable of mixing the samples and any reagents and also of conveying them toward a reading vessel in which the measurement will be taken. The fluorimeter of the invention preferably has a, numeric or alphanumeric, keypad allowing there to be input, for example, an identifier of a patient from whom there originates one or more samples for which the amount of nucleic acid included therein is to be calculated; at the end of the analysis, this identifier can be stated in a report printed using the printer. Moreover, it is possible to equip the fluorimeter with a system allowing reading of a bar code carried by a container containing the sample to be analysed. If the sample is contained in a container allowing measurement using the fluorimeter, such as a tray according to the invention, the bar code may include at least one production batch number for the container. This number may also be stated on the report printed using the printer at the end of the analysis.

The fluorimeter of the invention is preferably equipped with at least one means for supplying electric power, by mains or by battery (within a mobile use) and also at least one means for connecting to a computer system. If the fluorimeter is equipped with a plurality of connection means, these connection means will preferably be of several different standards. Within a mobile use, the fluorimeter is preferably as compact as possible, for example having the following dimensions: H<15 cm; L<25 cm; W<20 cm, and as light as possible so as to be able to be installed, without inconveniencing the user, for example on a laboratory benchtop, and to be able to be easily moved.

Finally, the fluorimeter is preferably equipped with a system allowing the transfer and mixing of reagents, in particular if said system is used with a tray according to the invention.

Tray

The tray according to the invention comprises all of the equipment and reagents required for the process according to the invention, i.e. the fluorophore optionally a diluent, a measuring vessel, a system for collecting the sample and anything indispensable for carrying out the process effectively.

With regard to the tray according to the invention, flexible materials are advantageously used to allow the mixture of the various reagents contained in the tray (sample, buffer, fluorophore) to be mixed, for example by pressure-vacuum or mechanic pressure.

The various compartments of the tray (wells, reservoirs, vessel) are preferably connected by capillaries and the passage from one compartment to another is preferably caused by crushing, for example, of the buffer reservoir, the fluorophore reservoir and/or the standardisation reservoir. The passage of the buffer through the fluorophore reservoir allows the fluorophore to be diluted and the mixture as a whole to be driven toward the vessel. The sample, which may or may not have been diluted beforehand, can be deposited in the well in the tray before or after the tray is positioned in a fluorimeter. Preferably, a precise sample volume is deposited in the well, then an optimally determined amount of the sample is directed, by way of the standardisation reservoir, toward the vessel in order to be mixed therein with the fluorophore. The mixing in the vessel can then be carried out, for example by subjecting the vessel to pressure-vacuum or mechanic pressure. The tray according to the invention is advantageous because it allows extemporaneous mixing of the fluorophore in a concentrated solution and of the buffer in order to arrive at the final dilution which is optimal for fluorescence; it also allows homogenisation of the fluorophore and the sample and also, if appropriate, suitable dilution of the sample and measurement of the emitted fluorescence.

DESCRIPTION OF THE FIGURES

FIG. 4: Fluorescence intensity of the DNA in a healthy-patient plasma with a PICOGREEN® dilution at 1/20,000, TBE 1× buffer (pH 8.4), delta-lambda=50 nm. The plasmas are diluted to 1/100. The y-axis represents the fluorescence intensity (UF) and the x-axis represents the emission wavelength (in nm).

FIG. 5: Fluorescence intensity of the DNA in a sick-patient plasma with a PICOGREEN® dilution at 1/20,000, TBE 1× buffer (pH 8.4), delta-lambda=50 nm. The plasmas are diluted to 1/100. The y-axis represents the fluorescence intensity (UF) and the x-axis represents the emission wavelength (in nm).

Figure 1:
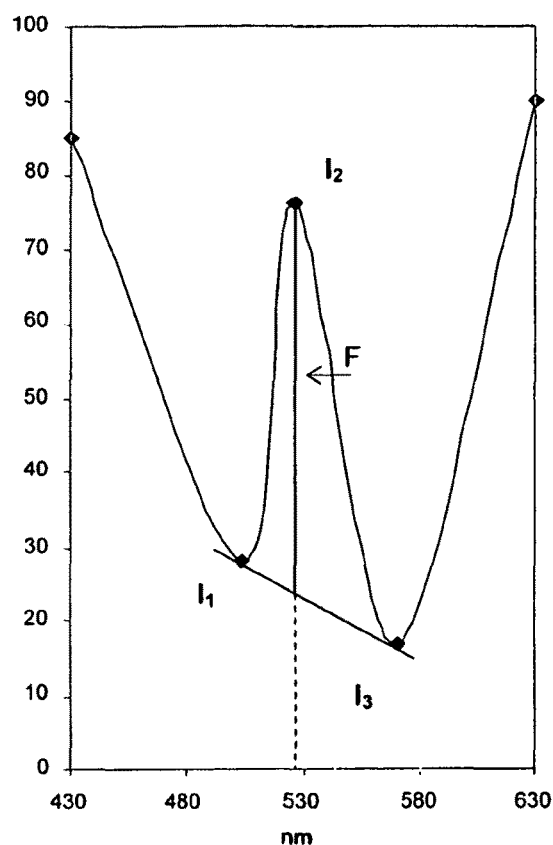
FIG. 1: Synchronous fluorescence spectrum of the DNA contained in plasma diluted to 1/100. The y-axis represents the fluorescence intensity (UF) and the x-axis represents the emission wavelength (in nm).

The invention will be described in greater detail with reference to the following example given merely by way of illustration and without entailing any limitation.

Example

Equipment

Plasmas or serums collected in herparinised EDTA tubes from centrifuged whole blood, then decanted; TBE 1× buffers (pH 8.5) (Tris 90 mM, boric acid 90 nM, EDTA 2 mM); polyethylene haemolysis tubes, acrylic vessels; synchronous fluorimeter (Shimadzu RF 535 reader, DR-3 data analyser); Picogreen® (dsDNA quantitation kit, Molecular Probes); standard DNA of known concentration for the standard range.

Method

A—Principle of Synchronous Fluorimetry a) Difficulties Associated with Conventional Fluorimetry The main difficulty often associated with conventional fluorimetric detection is related to the Rayleigh scattering resulting from the proximity of the excitation and emission wavelength. This effect can be particularly intensive in the case of analysis of complex and proteinated media such as blood serum.

When determining a conventional fluorescence spectrum, one of the monochromators will sweep the spectrum while the second remains fixed. In order to produce an emission spectrum, an excitation wavelength is chosen (480 nm for PICOGREEN® and the monochrometer which selects the re-emitted light will sweep beyond this limit, for example 480 to 620 nm.

When, at the start of the measurement, the two monochromators are set to the same wavelength, the emission monochrometer receives from the vessel containing the sample a very powerful light signal corresponding to the light scattered by the molecule of compounds in solution. During the scattering, the light, which is slightly polychromatic, has at least the same wavelength as that of the excitation light and therefore interferes with the measurement of the intensity of the emission light. Indeed, in the phenomenon of fluorescence, the excitation light is not monochromatic but rather corresponds to a set of wavelengths selected by the excitation monochromator: a monochromatic light will irradiate the reading vessel. The fluorescence light then emitted by the sample in solution is polychromatic and corresponds to a set of wavelengths. This scattered light will be selected by the emission monochromator and measured. When the two monochromators, the excitation monochromator and the emission monochromator are set to the same wavelength, the two types of light, scattered light and emission light, will be measured. It is impossible to measure the intensity of the emission light. This is Rayleigh interference.

This scattered light has an intensity much greater than that of the light emitted by fluorescence and is therefore able to mask it, thus rendering any determination arbitrary or even impossible. It is necessary to measure the intensity of the light emitted at a wavelength sufficiently remote from the excitation wavelength in order not to be troubled by this interference. It is therefore impossible under these conditions precisely to measure a signal derived from very closely related wavelengths.

In order to eliminate this parasitic phenomenon in conventional fluorescence it is necessary:
  either to reduce the width of the optical slits in order to reduce the coverage thereof (although this reduces the intensity of the light beams and therefore necessarily the sensitivity of the analysis);
  or to displace the excitation wavelength (although this reduces the fluorescence yield of the excited molecule and therefore, again, reduces the sensitivity of the analysis).

b) Contribution of Synchronous Fluorimetry
Principle of the Method

During the production of a synchronous spectrum, the spectrofluorimeter moves the two monochromators simultaneously. In this case, it is no longer a question of producing either an excitation spectrum or an emission spectrum but rather of measuring a set of signals corresponding to excitation light and emission light, the wavelengths of which are set apart from each other by a constant interval (named delta-lambda; 30 nm in the present case).

Advantages
1) Elimination of the Interference Resulting from Rayleigh Scattering The two monochromators will sweep the spectrum while moving at the same speed, offset by a constant interval. In this case, it is no longer possible to be troubled by Rayleigh scattering as the monochromators will never be at the same wavelength. Partial coverage of the slits in the excitation and emission optical systems may cause residual interference. However, the intensity of this interference is almost constant during the analysis and appears as a linear background on the spectrum. It is easily eliminated when measuring, by the method of the tangents, the height of the specific signal.

2) Reduction in the Width of the Band

If the excitation and emission wavelengths used during measurement are wavelengths which allow the peak yield of fluorescence, the re-emitted intensity will be at a peak. On the other hand, on moving away from these wavelengths, the intensity of the re-emitted light is weaker because the intensity of the absorbed light diminishes during excitation and the yield of fluorescence diminishes during emission. During synchronous fluorescence, the two phenomena are totaled and the variations in the re-emitted light are greater. This leads to a reduction in the width of the emission bands over the spectrum relative to those obtained in a conventional spectrum.

B—Measuring the Specific Fluorescence at Three Wavelengths

The foregoing remark enables a technique derived from the synchronous fluorescence technique to be extrapolated. The inventors have found on several hundreds of DNA measurements taken from as many different sick patients, that the trough observed in the synchronous spectrum were always present and, in particular, always had a minimum at the same wavelength.

Therefore, three important points can be noted on the synchronous spectrum shown in FIG. 1: the two inflection points "$I_1$" at 504 nm and "$I_3$" at 570 nm. The intensity of fluorescence "F" (in arbitrary units) is calculated by joining the two points $I_1$ and $I_3$, then the intensity of fluorescence is determined at the emission peak at 526 nm by measuring the mere height of the peak up to the intersection of the straight line "$I_1 I_3$". The height of the signal below the straight line $I_1 I_3$ corresponds to the interfering signal due to the Rayleigh scattering and is not measured.

This technique which is known as the tangent technique enables the background noise due to the Rayleigh scattering to be eliminated and gives a very good approximation of the fluorescence signal.

The inventors have therefore concluded from this that it was possible to develop a new technique at just these three fluorescence emission wavelengths.

The following measurements are therefore taken:
Emission $I_1$: $\lambda'_1 = 472$ nm $\lambda_1 = 502$ nm
Emission $I_2$: $\lambda'_2 = 496$ nm $\lambda_2 = 526$ nm
Emission $I_3$: $\lambda'_3 = 538$ nm $\lambda_3 = 568$ nm It is then necessary to extrapolate the fluorescence value "$I_R$" due to the Rayleigh effect at the main reading wavelength ($\lambda_2 = 526$ nm). This fluorescence is calculated on the basis of the measurements $I_1$ and $I_3$. As the fluorescence peak is not perfectly symmetrical, the fluorescence $I_R$ will be calculated according to the following formula:

$$(0.6 \times I_1) + (0.4 \times I_3) = I_R$$

The fluorescence specific to the DNA "F" will then be calculated on the basis of the measurement $I_R$ at the main wavelength in the following manner:

$$F = I_2 - I_R$$

Figure 14:
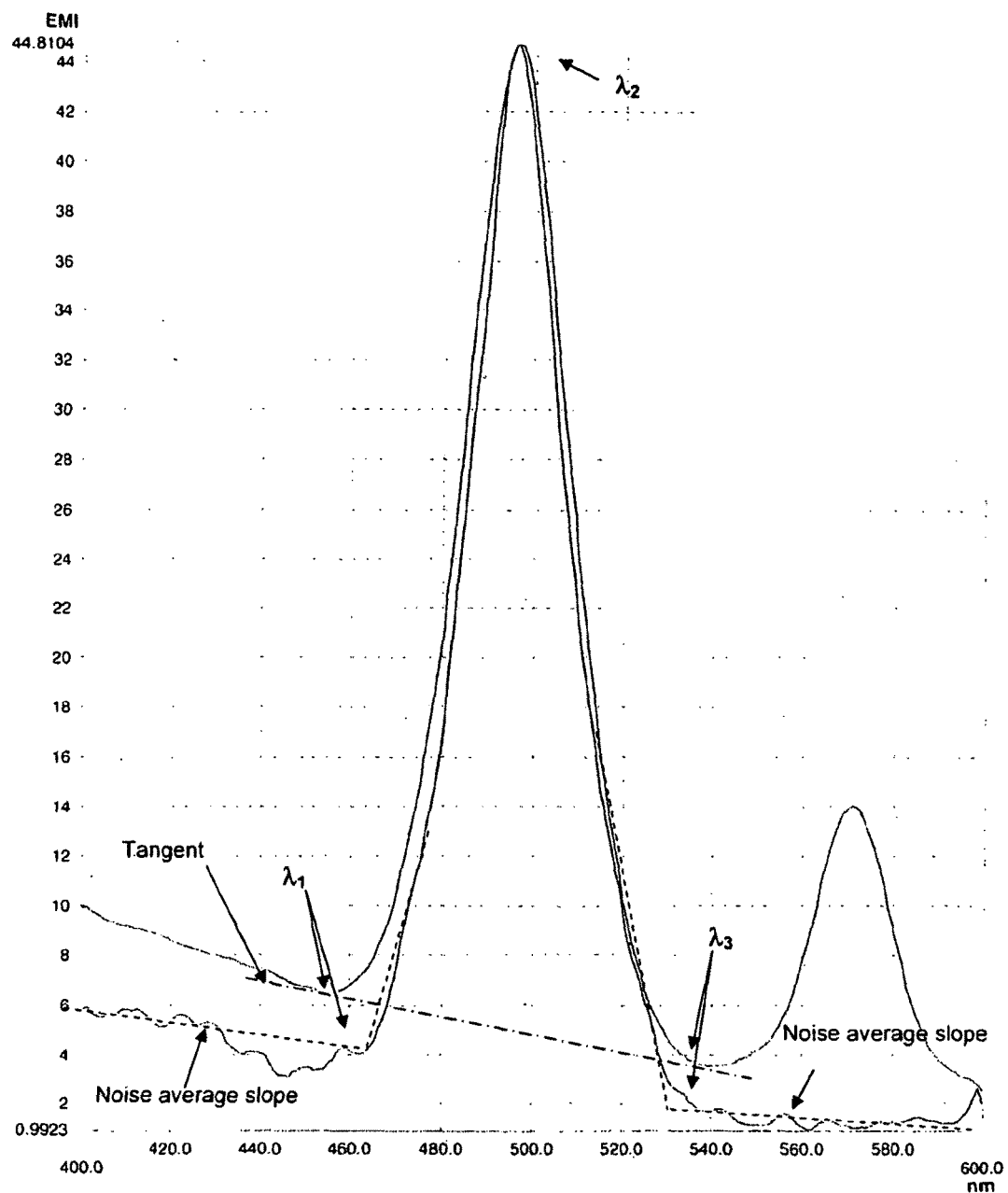
FIG. 14: Synchronous spectrum of DNA in a plasma with PICOGREEN® dilution to 1/20,000, TBE 1× buffer (pH 8.4) measured using a Shimadzu RF 535 spectro fluorimeter (top curve) and Safas Xenius spectro fluorimeter (bottom curve). The plasmas are diluted to 1/100. The y-axis represents the fluorescence intensity (UF) and the x-axis represents the emission wavelength (in nm). The graphical methods for determining $\lambda_1$, $\lambda_2$, and $\lambda_3$ are represented.
Figure 15:
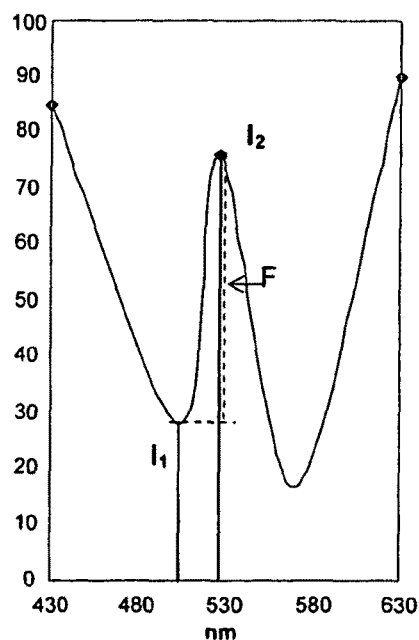
FIGS. 15 and 16 represent examples of fluorescence (F) determination with the method according to the invention using fluorescence intensities ($I_1$, $I_2$) at two wavelengths.
Figure 16:
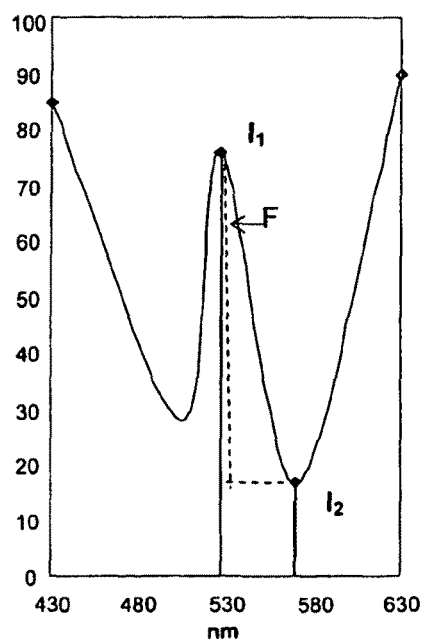

FIG. 14 shows that this method of determining the fluorescence can be generalised independently of the spectrofluorimeter used.

C—Mode of Operation
Preparation of PICOGREEN®.

The stock solution of PICOGREEN® diluted 50 times in a 50% mixture of ethynol/TBE (v/v) is aliquoted (120 μl) in Eppendorf® tubes and then stored in a freezer at −20° C. in the absence of light.

Experiment Design

The aliquoted plasmas stored in the freezer (at −20° C.) are thawed and brought to the ambient temperature of the laboratory (between 15 and 25° C.), and are then diluted (by a factor of 10 to 300) in the TBE 1× buffer (final volume=450 µl. These dilutions are stored in ice until the analysis.

40 ml of the TBE 1× buffer are pipetted, and 100 µl of extemporaneously thawed PICOGREEN® are then added to them (resulting in a final dilution factor of 20,000), the mixture being stored in ice in the absence of light.

The spectrofluorimeter is onset at least 20 to 30 minutes before the beginning of the measurements is programmed as follows:
the monochromator will scan from 400 to 600 nm during excitation;
the monochromator will scan from 430 to 630 nm during emission.

In order to take the measurements, the following procedure is adopted:
1. 9 ml of PICOGREEN® diluted to 1/20,000 are taken and transferred into a haemolysis tube which is placed in the absence of light on the bench;
100 µl of the dilution of plasma/serum (Final volume=2 ml), are then added, the mixture is vortexed for 8 to 12 seconds and is left on the bench for 2 to 3 minutes, after which the mixture is rapidly pumped into an acrylic cuvette to begin registration of the spectrum.

A standard range is always made on the basis of the standard DNA of known concentration provided with the PICOGREEN®, the range points selected being: 2.5 ng; 25 ng and 50 ng/ml.

N.B. The TBE 1× buffer should be prepared at least 24 h before the measurements and should be kept on the bench as it significantly reduces the Rayleigh scattering phenomena.

D—Results
A—Perfecting the Experimental Conditions
1—Choice of Buffer

As PICOGREEN® fits in the double helix of DNA, between the bases, the nature of the buffer should influence the fluorescence signal. Various types of buffer commonly found in the laboratories were therefore tested.

TBE 1× buffer (tris(hydroxymethylamine) aminomethane 1 M, EDTA 0.1 mM, pH=7.5): conventional buffer for use of PICOGREEN®.

10 mM monopotassium phosphate buffer, pH=7.8: the phosphate buffer has significant fluorescence which makes it impossible to measure the concentrations of DNA present in the standards or the plasma with adequate precision.

TBE 1× buffer (90 mM tris(hydroxymethylamine) aminomethane, 90 mM boric acid, 2 mM EDTA, pH=8.5); the buffer TBE 1× has slight residual fluorescence but in particular it does not have a fluorescence peak at the test wavelength. Its use is therefore advantageous in the analysis according to the invention.

2—Choice of pH

The three foregoing buffers were tested at various pHs: 5, 5.5, 6, 6.5, 7, 7.5, 8 and 8.5.

The variations in pH in these zones do not modify the fluorescence spectra.

3—Choice of Dilution of the Reagent: PICOGREEN®.

The fluorimetric techniques are carried out in an extremely dilute medium in order to limit the conventional interference phenomena: auto inhibition, quenching, fading and competition, to which Rayleigh scattering is added.

The inventors determined the lowest concentration of reagent which gives the most intense signal.

The following concentrations of PICOGREEN® were tested: 1/100, 1/250, 1/500, 1/1,000, 1/2,000, 1/4,000, 1/8,000, 1/12,000, 1/20,000.

A weaker dilution gives signals of weaker intensity. An excessively strong dilution gives signals which are much less repeatable and have non proportional growth at the tested DNA concentration.

Figure 2:
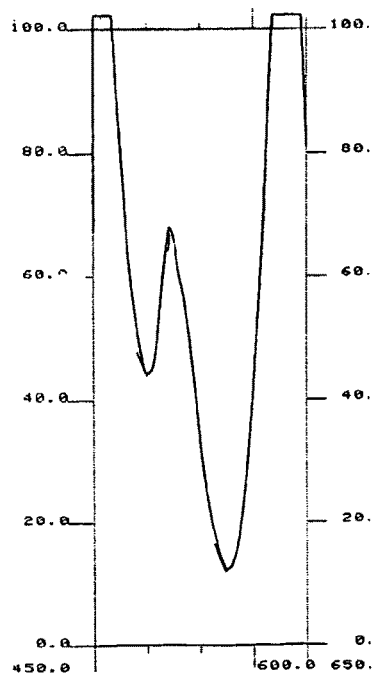
FIG. 2: Fluorescence intensity of the DNA in a healthy-patient plasma with a PICOGREEN® dilution at 1/4,000, TBE 1× buffer (pH 8.4), delta-lambda=50 nm. The plasmas are diluted to 1/100. The y-axis represents the fluorescence intensity (UF) and the x-axis represents the emission wavelength (in nm).
Figure 3:
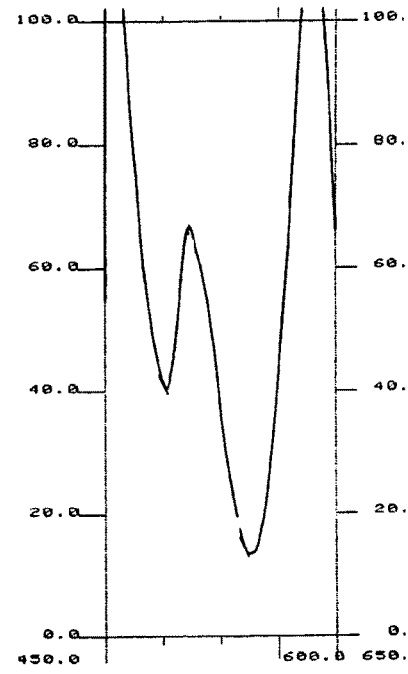
FIG. 3: Fluorescence intensity of the DNA in a sick-patient plasma with a PICOGREEN® dilution at 1/4,000, TBE 1× buffer (pH 8.4), delta-lambda=50 nm. The plasmas are diluted to 1/100. The y-axis represents the fluorescence intensity (UF) and the x-axis represents the emission wavelength (in nm).

The signals become detectable as from a dilution of 1/4,000, but the technique lacks sensitivity. At this dilution, it is not possible to distinguish between a control plasma (FIG. 2) and a sick patient's plasma (FIG. 3).

The best results are found for a PICOGREEN® dilution of 1/20,000. At this reagent dilution, the technique appears sensitive and linear and it is possible to distinguish between a control plasma (FIG. 4) and a sick patient's plasma (FIG. 5).

4—Choice of Plasma Dilution

To avoid the interference associated with the biological matrix it is important to work with samples which are as strongly diluted as possible. Plasmas diluted to 1/20, 1/50/1/100, 1/150, 1/200, 1/300, 1/400 were used.

The best results are obtained with plasmas diluted to 1/100.

No haze associated with the turbidity of the plasmas, even in the case of opalescent or cloudy plasmas, or associated with haemolysis, icterus or hyperprotidemia was observed.

This dilution allows the control plasmas to be measured with adequate precision.

5—Choice of Wavelength Difference Between the Excitation Light and the Emission Light The peak excitation and emission wavelengths proposed by the manufacturer of PICOGREEN® are 485 and 530 nm respectively. The choices of these wavelengths and of their difference of 45 nm may be due to the properties of the molecule, but also to the material stresses associated with the scattering of light in the reading vessel. The choice of a difference of 45 nm may originate from technical stresses associated with the large majority of fluorimeters which are only capable of limiting the Rayleigh interference when the excitation and the emission wavelengths are separated by 40 nm.

If this were the case, they would not be peak fluorescence wavelengths but compromise wavelengths between the best sensitivity and the least interference.

The use of synchronous fluorescence, while considerably limiting the Rayleigh interference, allows molecules having peak fluorescence wavelengths which can be separated by less than 10 nm to be used.

Differences of 20, 25, 30, 35, 40, 45, 50 and 55 nm were therefore tested.

Figure 6:
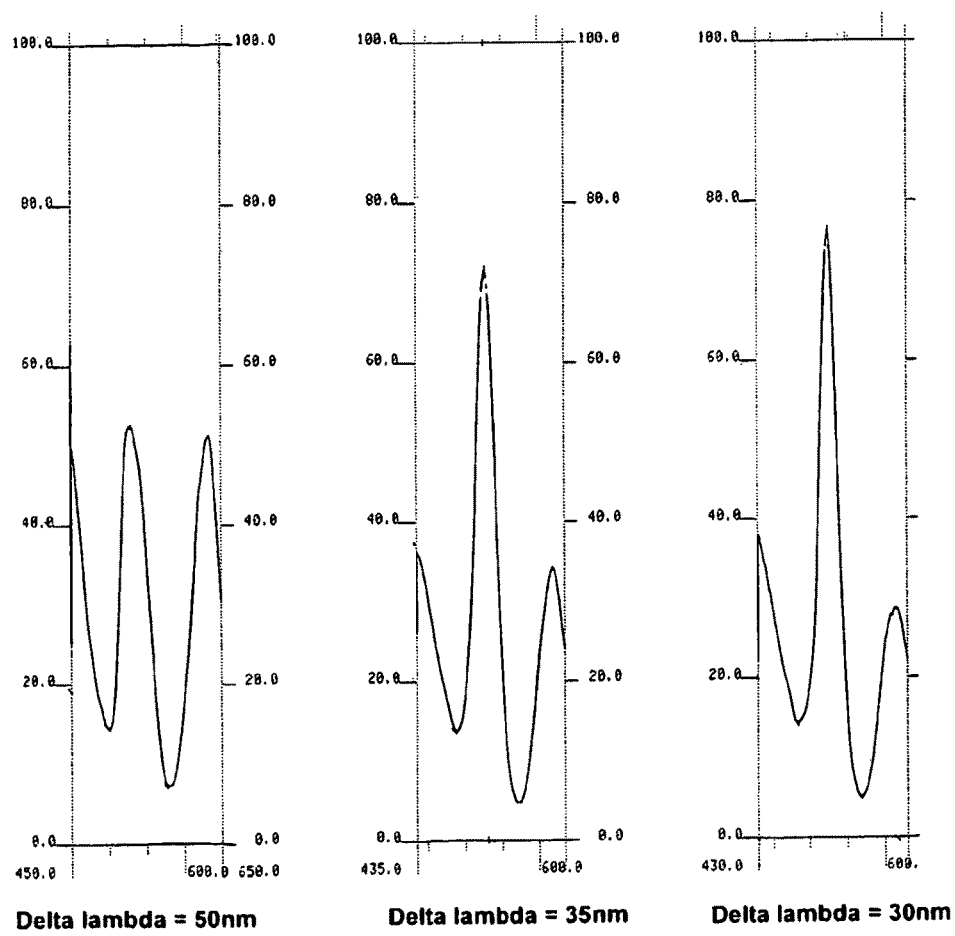
FIG. 6: Fluorescence intensity of the plasma DNA at three different delta-lambdas (50 nm, 35 nm and 30 nm), TBE 1× buffer (pH 8.4). The y-axis represents the fluorescence intensity (UF) and the x-axis represents the emission wavelength (in nm).

The best sensitivity was obtained with a difference between the excitation wavelength and emission wavelength of 30 nm (FIG. 6).

6—Stability of PICOGREEN® Over Time

The repeatability of the measurements is as follows:

| Conc ng/ml | 5 |
|---|---|
| Average | 4.5 |
| Standard deviation | 0.026 |
| CV % | 0.59 |

CV % = (standard deviation/average) × 100

Their reproducibility is as follows:

| Conc ng/ml | 2 | 60 |
|---|---|---|
| Average | 5.1 | 66.85 |
| Standard deviation | 0.9 | 2.96 |
| CV % | 5.57 | 4.43 |

The accuracy of the technique is acceptable for use in clinical biology.

b—Quality of the Synchronous Fluorescence Technique

1—Accuracy

The precision includes repeatability and reproducibility tests.

Repeatability

The test was carried out by measuring 10 times the same day with the same preparation of reagents on the various types of sample.

The inventors used three standards of different concentrations as well as two samples of patients' plasma: the first was frozen for a week and the second was analysed as fresh plasma.

The results expressed in CV % ((standard deviation/average)*100) are compiled in the following table:

| Type of sample | CV % |
| --- | --- |
| Standard 1 (5 ng/ml) | 6.7 |
| Standard 2 (50 ng/ml) | 2.4 |
| Standard 3 (100 ng/ml) | 2.3 |
| Patient 1 (frozen) (215 ng/ml) | 2.8 |
| Patient 2 (fresh) (1,110 ng/ml) | 3.5 |

Reproducibility

The test was carried out by analysing 20 times on 20 different days with reagents which were reconstituted each day.

The inventors used three standards of different concentrations as well as a sample of plasma which was frozen in aliquots.

The results are compiled in the following table:

| Type of sample | CV % |
| --- | --- |
| Standard 1 (5 ng/ml) | 15 |
| Standard 2 (50 ng/ml) | 2.4 |
| Standard 3 (100 ng/ml) | 5.9 |
| Patient 1 (frozen) (245 ng/ml) | 4.8 |

2—Accuracy

The test was carried out in the following manner. Two purified samples of DNA were analysed by a photometric technique (260 nm) (corrected by the presence of RNA or proteins). These measured values serve as a reference for the analysis. These purified samples of DNA were then analysed by the method of synchronous fluorimetry.

The following table shows the accuracy of the method expressed as a percentage of DNA found relative to the photometric method.

| Concentration in ng/ml | % accuracy |
| --- | --- |
| 15 | 102 |
| 77 | 106 |
| 159 | 93 |

3—Detection Threshold

The detection threshold is calculated in the following manner. 20 examples containing only the TBE 1× buffer were measured. The average of these ten determinations was then calculated, and three times the standard deviation of the measurements obtained was added to this average.

The threshold measured in this way is 3.5 ng/ml.

4—Sensitivity Threshold

The first DNA concentration detectable with adequate precision of 20% is 4 ng/ml. It is found to be relatively satisfactory. The plasma concentration of a healthy subject is approximately 2 to 6 ng/ml of circulating DNA. In the hospital, the pathological values are very much higher than these normal values.

5—Linearity Test

Figure 7:
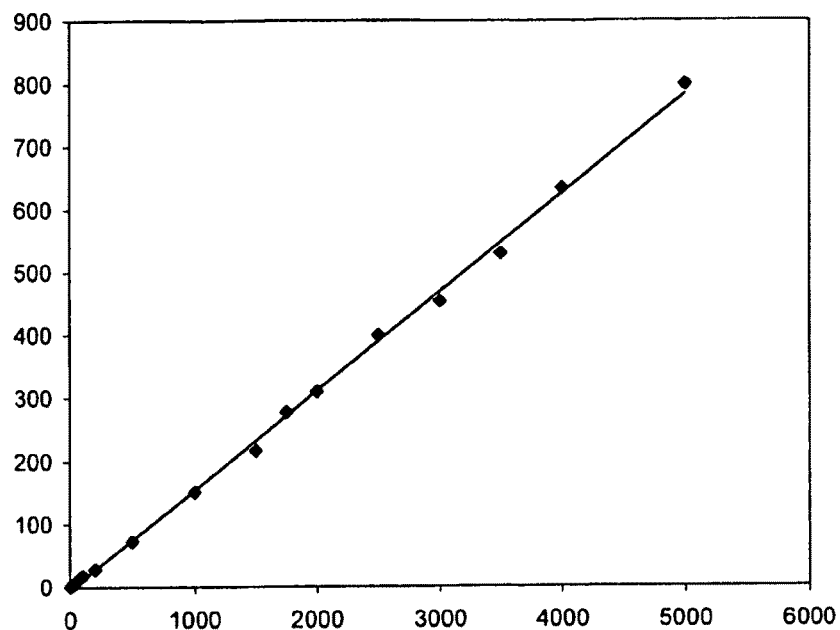
FIG. 7: Linearity of the fluorescence intensity (y-axis, any desired units) as a function of the DNA concentration (x-axis, ng/ml).
Figure 13:
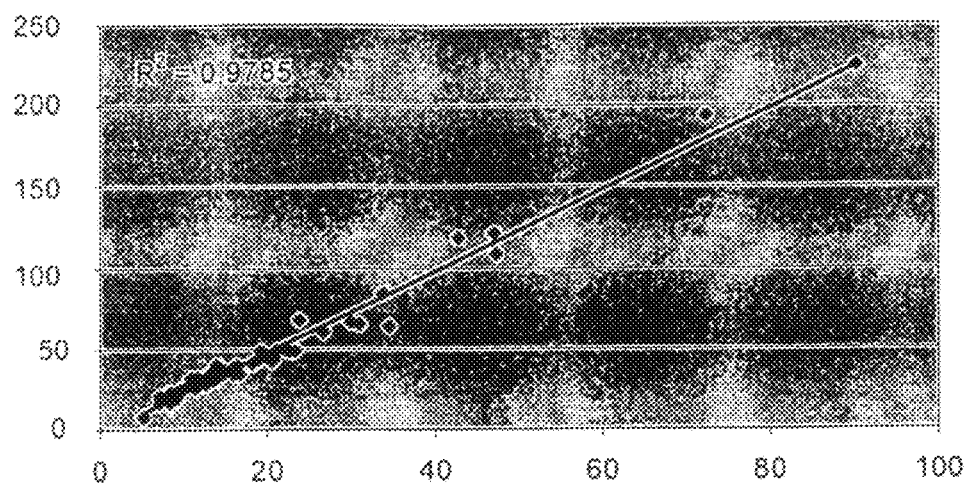
FIG. 13: Correlation between the DNA concentration measured using synchronous fluorimetry (y-axis, number of copies/ml) and using three-wavelength or differential fluorimetry (x-axis, ng/ml) on the plasma DNA obtained, without preparing the sample, from patients suffering from prostate cancer, TBE 1× buffer (pH 8.4) PICOGREEN® diluted to 1/20,000.

From 4 ng/ml of DNA, the technique is linear up to at least 5,000 ng/ml (FIG. 7).

c—Quality of the Technique Involving Measurement of the Three Fluorescence Points The results obtained by this method are identical in all points to those of the synchronous fluorescence technique (FIG. 13).

Conclusion: these first tests show that the synchronous fluorimetry methods or methods involving measurement of the three fluorescence points are reliable techniques which can be used in clinical biology.

These results are compared hereinafter with those of quantitative PCR.

d—Determination of Circulating DNA by the Synchronous Fluorimetry Method in Various Cancers (Prostate, Colon)

In a first stage, work was carried out on identical DNA extracts in order to validate the method on purified extracts and check its relevance relative to the reference analysis: quantitative PCR. Then, in a second stage, this method was validated directly on the plasma of patients, always by comparison with the reference technique.

Figure 8:
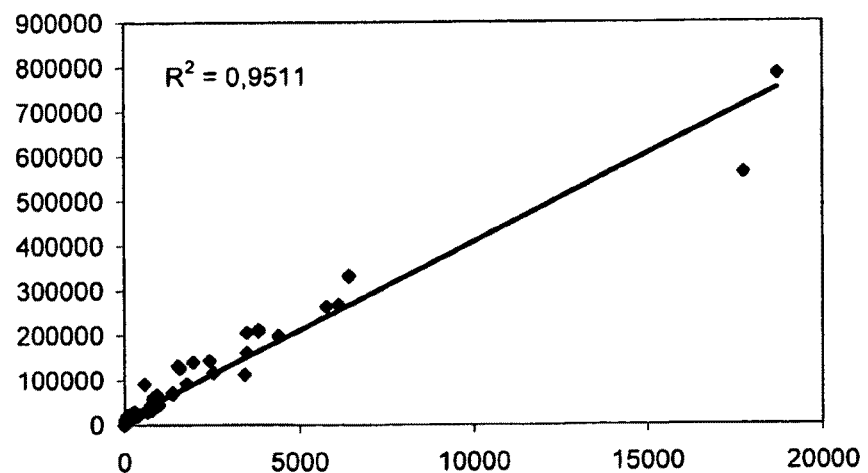
FIG. 8: Correlation between the DNA concentration measured using synchronous fluorimetry (y-axis, number of copies/nil) and using real-time PCR (x-axis, number of copies/ml) on DNA extracted using kits from patients suffering from prostate cancer, TBE 1× buffer (pH 8.4) PICOGREEN® diluted to 1/20,000.

1—Correlation of PCR Versus Fluorimetry on Extracted DNA Using a Kit in Various Cancers Prostate Cancer The correlation is excellent, but a deformation of the cloud of points is observed at low DNA concentrations (FIG. 8).

Figure 9:
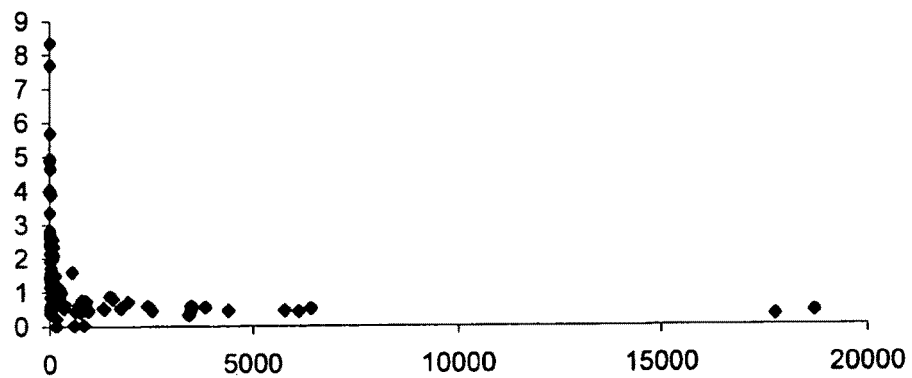
FIG. 9: Relationship between the number of copies measured by real-time PCR and that measured by synchronous fluorimetry as a function of the number of copies obtained by real-time PCR, from the results represented in FIG. 8.

This deformation is analysed by the graph of the ratios between the results presented in FIG. 9. A pronounced deformation is of the point cloud is observed. Below a value of 100 copies of genome/ml, the PCR technique appears to lack sensitivity, contrary to synchronous fluorimetry.

Figure 10:
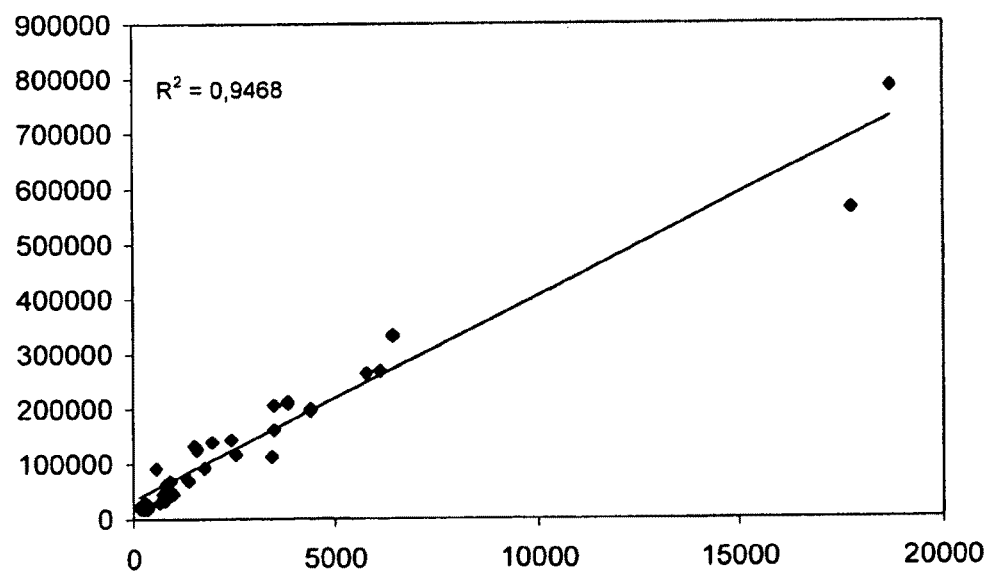
FIG. 10: Correlation between the DNA concentration measured using synchronous fluorimetry (y-axis, number of copies/ml) and using real-time PCR (x-axis, number of copies/ml) on DNA extracted using kits from patients suffering from prostate cancer, TBE 1× buffer (pH 8.4), PICOGREEN® diluted to 1/20,000; only the concentrations of DNA extracted from patients for whom the genome copy number/ml is greater than 100 have been preserved relative to the results presented in FIG. 8.

Beyond this threshold of 100 copies of genome/ml, the correlation remains excellent (FIG. 10).

Prostate and Colon Cancers at Differing Stages

Figure 11:
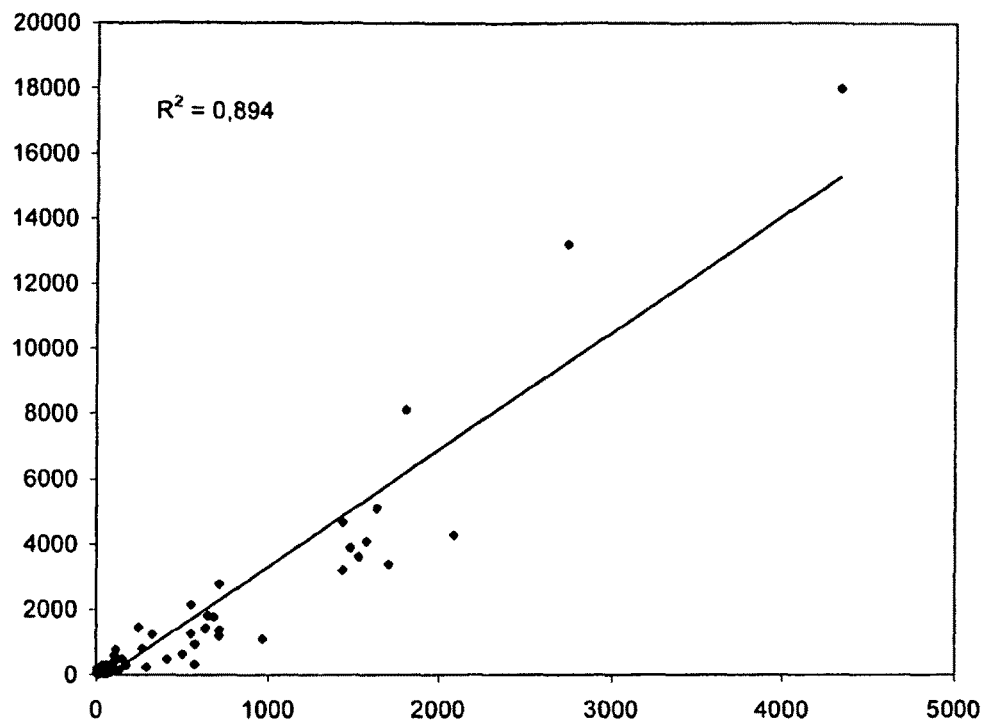
FIG. 11: Correlation between the DNA concentration measured using real-time PCR (y-axis, number of copies/ml) and using synchronous fluorimetry (x-axis, number of copies/ml) on DNA purified from patients suffering from prostate and colon cancers, TBE 1× buffer (pH 8.4), PICOGREEN® diluted to 1/20,000.

A second series of measurements was taken on samples from sick patients presenting either prostate cancers or colon cancers. As in the previous series, the threshold of 100 copies of genome/ml is found with the quantitative PCR technique (FIG. 11).

2—Correlation of PCR Versus Fluorimetry on Plasma DNA

Figure 12:
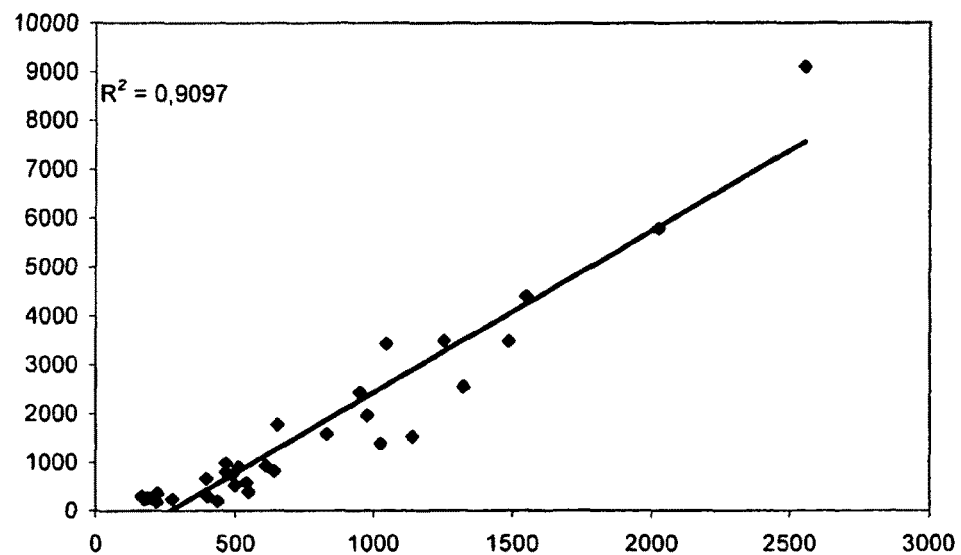
FIG. 12: correlation between the DNA concentration measured using real-time PCR (y-axis, number of copies/ml) and using synchronous fluorimetry (x-axis, number of copies/ml) on plasma DNA obtained, without preparing the sample, from patients suffering from prostate cancer, having a genome copy number/ml greater than 100. TBE 1× buffer (pH 8.4), PICOGREEN® diluted to 1/20,000.

The investigation was also validated on biological samples which had not been subjected to preparation. The inventors used frozen plasmas from patients suffering from cancer of the prostate or the colon. Samples having a number of copies of genome≥100 copies/ml (n=32) were more particularly used and the DNA was quantified directly in the plasma. (FIG. 12).

It is observed that the correlation is excellent and at the same level as that obtained with the extracted DNA.

e—Determination of the Circulating DNA by the Method Involving Three Points of Fluorescence in Various Cancers (Prostate, Colon)

Simultaneously with the measurement by synchronous fluorimetry, the inventors analysed, by the method involving three points of fluorescence, the circulating DNA concentration in each of the plasmas measured without prior preparation of the DNA (FIG. 13).

It is found that the correlation is excellent and completely identical to that obtained with synchronous fluorescence. The two new techniques for determining the circulating DNA are therefore completely equivalent and perfectly correlated with the reference technique: quantitative PCR.

Discussion

Quantitative PCR is currently the most widely used method for measuring the quantity of circulating DNA. However, this method is relatively expensive, specialised and unsuitable for use in medical emergency centres.

Owing to its very principle, PCR very significantly amplifies all the DNA present in the sample. It has very great difficulty in distinguishing between samples from patients presenting slight variations in their DNA concentration because they will be amplified in almost identical proportions. In this case, however, the PCR technique lacks sensitivity. Patients should present clear increases in their DNA concentration in order to be distinguished from the controls or distinguished from one another.

In quantitative PCR, moreover, fluorescence is measured in a complex reaction medium which is rich in enzymes and macromolecules (primers, purified DNA fragment, fluorophore, etc.) which risk inducing significant interference in the analysis. It is known that, the more concentrated medium, the less powerful the fluorescence reading. In this context, the main types of interference possible are as follows:

Autoinhibition. There may be autoinhibition of the fluorescence at strong concentrations, owing to the increase in the number of collisions between the molecules which dissipate the energy received or owing to the formation of non-fluorescent polymers.

Inhibition of fluorescent or quenching. In a highly concentrated or heterogeneous complex medium there is also a risk of having a fluorescence or quenching inhibition phenomenon, as a result of an interaction between the fluorescent molecule and the solvent or another solute. The yield of fluorescence and/or the duration of fluorescence are diminished. From a practical point of view, this means that the compound is less fluorescent when it is in the presence of an inhibiting substance. This is one of the drawbacks during an analysis in a biological medium which has not been purified beforehand. In addition, extinction is not always uniform.

Fading (photo bleaching). This is the loss of fluorescence of the fluorochrome due to the hyperexcitation of the light which leads to the destruction of the molecule or to the absence of its reaction by coupling of its reactive form with another molecule.

Competition. This is due to the auto fluorescence of specific substances or contaminants of the glassware.

In quantitative PCR, if the DNA is analysed at approximately the same concentration as with the synchronous fluorescence technique, the fluorophore is 1,000 times more concentrated therein. In addition, the molecules of primer and of polymerases are at adequate concentrations to interfere themselves with the emitted light.

This strong concentration of molecules in the medium also promotes the Rayleigh effect associated with the dispersion of the incident light by the molecules in solutions. The closer the excitation and emission wavelengths, which are separated by only 45 nm, the more sensitive this is, leading to significant technical constraints in the choice of the intensity of the lamp and the choice of the reading slots.

All these elements led the inventors to think of a new technique based on an analysis in a much more dilute medium.

The choice of a conventional fluorescence technique considerably increases the sensitivity of the analysis and avoids the phases of extraction and amplification, which entail the most risk of interference, technical variability and handling errors.

The choice of synchronous fluorimetry ensures excellent specificity of the analysis and, by allowing the use of peak excitation emission wavelengths, allows the further increase in the sensitivity of the analysis.

Implementation of this method revealed the existence of three key points in the synchronous spectrum. Analysis of all the data also assured the inventors of the stability of these points. They are always present and always at the same wavelengths. A new measurement strategy was therefore developed by measuring only three fluorescence intensities and developing a calculation formula for precisely measuring the fluorescence specific to DNA. This new technique has the same excellent analytical qualities as that developed in synchronous fluorimetry, in particular with regard to its sensitivity.

Better sensitivity of the DNA analysis allows earlier detection of the increases in the follow-up of the patients. This is particularly true in the case of elderly subjects (>65 years) where it seems (data not shown) that the normal values increase progressively with age. This will probably allow the field of application of this analysis to be extended.

The techniques developed are very satisfactory. They are highly precise and the analysed range is well adapted to clinical requirements. In addition, they are very well correlated with the most commonly used technique: real time quantitative PCR. The various correlations carried out demonstrate the excellent clinical relevance of our results. The threshold of 100 copies of genome/ml is close to that of 150 copies of genome/ml which is currently the threshold of pathological decision in quantitative PCR. This corresponds approximately to 15,000 copies of genome/ml of DNA by our technique, this being the value which is also found in the literature.

The inventors have therefore been able to define two new techniques for eliminating the stages of DNA extraction and amplification, and this has allowed a considerable reduction in the analysis time to a few minutes.

REFERENCES

Anker P. et al. *Detection of Circulating Tumour DNA in the blood (plasma/serum) of Cancer Patients*. Cancer Metastasis Rev 1999, 18:65-73.

Boddy J. L. et al. *Prospective Study of Quantitation of plasma DNA Levels in Diagnosis of Malignant versus Benign Prostate Disease*. Clinical Cancer Res 2005, 11:1394-1399.

Chang C. P. *Elevated cell-free serum DNA detected in patients with myocardial infarction*. Clin Chim Acta 2003, 327:95-101.

De Kok J B et al. *Detection of Tumour DNA in Serum of Colorectal Cancer Patients*. Scand J Lab Clin Invest 1997, 57:601-4.

Fournié G. J. et al. *Plasma DNA as a Marker of Cancerous Cell Death: Investigation in Patients Suffering from Lung Cancer in Nude Mice Bearning Human Tumours*. Cancer Letters 1995, 91:221-227.

Gal S. et al. *Quantitation of Circulating DNA in Serum of Breast Cancer Patients by Real Time PCR*. British Journal of Cancer 2004, 90:1211-1215.

Greenstock C. L., et al. *Interaction of ethidium bromide with DNA as studied by kinetic spectrophotometry*. Chem Biol Interact. 1975, 11:441-7.

Jahr S et al. *DNA Fragments in the blood Plasma of Cancer Patients: Quantitation and Evidence for their Origin from Apoptotic and Necrotic Cells.* Cancer Res 2001, 61:1659-65.

Jung K. et al. *Increased Cell Free DNA in Plasma of Patients with Metastasic Spread in Prostate Cancer.* Cancer letters 2004, 205:173-180.

Lam N. Y. et al. *Time Course of Early and Late Changes in Plasma DNA in Trauma Patients.* Clinical Chemistry 2003, 49:1286-1291.

Leon S A, et al. *Radioimmunoassay for nanogram quantities of DNA.* J Immunol Methods 1975 9:157-64.

Leon S. et al. *Free DNA in the Serum of Cancer patients and effects of the Therapy.* Cancer Res. 1977, 37:646-650.

Mandel P, and Metais P. *Les acides nucléiques du plasma sanguin chez l'homme.* C. R. Soc Biol 1948, 142:241.

Mulder J. *Rapid and simple PCR assay for quantitation of human immunodeficiency virus type 1 RNA in plasma: application to acute retroviral infection.* J Clin Microbiol 1994, 32:292-300.

Shao Z et al. *P53 Mutation in Plasma DNA and its Prognostic Value in Breast Cancer Patients.* Clinical Cancer Res 2001, 7:2222-2227.

Shapiro B. et al. *Determination of Circulating DNA Levels in the Patients with Benign or malignant Gastrointestinal Disease.* Cancer 1983, 51:2116-2120.

Siebert P D, et al. *Competitive PCR.* Nature. 1992, 359:557-8.

Sozzi G. et al. *Analysis of Circulating Tumour DNA in Plasma at Diagnosis and Follow-up Lung Cancer Patients.* Cancer Res 2001, 61:4675-4678.

Sozzi G. et al. *Quantitation of Free Circulating DNA as a Diagnostic Marker in Lung Cancer.* Journal of Clinical Oncology 2003, 21:3902-3908.

Tan E. M. et al. *Deoxyribonucleic acid (DNA) and antibodies to DNA in the serum of patients with systemic lupus erythematosus.* J Clin Invest 1966, 45:1732-40.

Thijssen M. A. et al. *Difference between Free Circulating Plasma and Serum DNA in Patients with Colorectal Liver Metastasis.* Anticancer Res 2002, 22:421-425.

Wu T. L. et al. *Cell Free DNA: Measurement in Various Carcinomas and Establishment of normal Reference range.* Clinica Chimica Acta 2002, 321:77-87.

Yap E P, et al. *Nonisotopic SSCP and competitive PCR for DNA quantification: p53 in breast cancer cells.* Nucleic Acids Res. 1992, 20:145.

The invention claimed is:

1. A method for determining the amount of nucleic acid present in a biological sample, comprising the steps of:
adding to the biological sample a single fluorophore capable of interacting with the nucleic acid wherein the fluorophore is ([N-bis-(3-dimethylaminopropyl)-amino]-4-[2,3-dihydro-3-methyl-(benzo-1,3-thiazol-2-yl)-methyllidene]-1-phenyl-quinolinium]+);
measuring fluorescence intensities, $I_1$, $I_2$ and, optionally $I_3$, emitted by the single fluorophore at at least two emission wavelengths, $\lambda_1$, $\lambda_2$ and, optionally a third emission wavelength $\lambda_3$, in response to light stimulations at at least two excitation wavelengths, $\lambda'_1$, $\lambda'_2$ and, optionally a third excitation wavelength $\lambda'_3$, respectively, wherein the difference (delta-lambda) between each excitation wavelength and corresponding emission wavelength is 30 nm;
deducing the amount of nucleic acid present in the sample from the at least two measured fluorescence intensities, wherein the deducing step comprises calculating a value F according to at least one of the formulas:

$$F = |I_2 - I_1| \text{ and/or } F = I_2 - \left[\frac{I_1 - I_3}{\lambda_1 - \lambda_3}\lambda_2 - \frac{\lambda_1 I_3 - \lambda_3 I_1}{\lambda_1 - \lambda_3}\right],$$

and determining the amount of nucleic acid in the sample from the value of F by using a calibration curve.

2. The method according to claim 1, wherein the nucleic acid is DNA or RNA.

3. The method according to claim 1, wherein the sample is is diluted from 1/20 to 1/400 in a buffer.

4. The method of claim 3, wherein the buffer is a TRIS-Borate-EDTA (TBE) buffer.

5. The method according to claim 1, wherein the sample originates from a patient and the method determines whether the patient has suffered cellular disruption of a physio-pathological origin.

6. The method according to claim 1, wherein the fluorophore is a nucleic acid intercalating agent.

7. The method according to claim 1, wherein the fluorescence intensities ($I_1$, $I_2$ and $I_3$), emitted by the fluorophore are measured at three emission wavelengths $\lambda_1$, $\lambda_2$ and $\lambda_3$ in response to light stimulations at three excitation wavelengths, $\lambda'_1$, $\lambda'_2$ and $\lambda'_3$, respectively, with $\lambda_1 < \lambda_2 < \lambda_3$ and $\lambda_1$, $\lambda_2$ and $\lambda_3$ being predetermined.

8. The method according to claim 7, wherein the amount of nucleic acid is deduced from the following value of F:

$$F = I_2 - \left[\frac{I_1 - I_3}{\lambda_1 - \lambda_3}\lambda_2 - \frac{\lambda_1 I_3 - \lambda_3 I_1}{\lambda_1 - \lambda_3}\right].$$

9. The method according to claim 8, wherein the amount of nucleic acid in the sample is deduced from the value of F using a calibration curve.

10. The method according to claim 7, wherein the fluorophore is ([N-bis-(3-dimethylaminopropyl)-amino]-4-[2,3-dihydro-3-methyl-(benzo-1,3-thiazol-2-yl)-methyllidene]-1-phenyl-quinolinium]+) and the wavelengths are as follows:
$\lambda'_1$=472±10 nm $\lambda_1$=502±10 nm
$\lambda'_2$=496±10 nm $\lambda_2$=526±10 nm
$\lambda'_3$=538±10 nm $\lambda_3$=568±10 nm.

11. The method according to claim 1, wherein the fluorescence intensities, $I_1$ and $I_2$, emitted by the fluorophore at two emission wavelengths $\lambda_1$ and $\lambda_2$ in response to light stimulations at two predetermined excitation wavelengths, $\lambda'_1$ and $\lambda'_2$, respectively are measured.

12. The method according to claim 11, wherein the amount of nucleic acid is deduced from the absolute value of the difference between $I_1$ and $I_2$, i.e. the following value of F:

$$F=|I_2-I_1|.$$

13. The method according to claim 11, wherein the fluorophore is ([N-bis-(3-dimethylaminopropyl)-amino]-4-[2,3-dihydro-3-methyl-(benzo-1,3-thiazol-2-yl)-methyllidene]-1-phenyl-quinolinium]+) and the wavelengths are as follows:
$\lambda'_1$=472±10 nm $\lambda_1$=502±10 nm, and
$\lambda'_2$=496±10 nm $\lambda_2$=526±10 nm, or
$\lambda'_1$=496±10 nm $\lambda_1$=526±10 nm, and
$\lambda'_2$=538±10 nm $\lambda_2$=568±10 nm.

14. The method of claim 1, wherein the biological sample is a serum or plasma sample from a patient.

15. The method of claim 14, wherein the patient is selected from the group consisting of a patient suffering or suspected of suffering from a cancer, a patient undergoing chemotherapy, a patient having undergone a surgical operation, a traumatised patient and a patient having undergone a myocardial infarction.

16. The method of claim 15, wherein the patient is a cancer patient.

17. The method of claim 14, further comprising obtaining a serum or plasma sample from the patient, wherein the method is performed without amplifying, purifying or isolating said nucleic acid in said sample.

18. The method of claim 1, wherein the method is performed without amplifying, purifying or isolating said nucleic acid in said sample.

* * * * *